(12) United States Patent
Reschiglian et al.

(10) Patent No.: US 8,263,359 B2
(45) Date of Patent: Sep. 11, 2012

(54) METHOD AND DEVICE TO FRACTIONATE STEM CELLS

(75) Inventors: Pierluigi Reschiglian, Ferrara (IT); Barbara Roda, Bologna (IT); Gian Paolo Bagnara, Bologna (IT); Andrea Zattoni, Bologna (IT)

(73) Assignee: Alma Mater Studiorum—Universita di Bologna, Bologna (IT)

( * ) Notice: Subject to any disclaimer, the term of this patent is extended or adjusted under 35 U.S.C. 154(b) by 798 days.

(21) Appl. No.: 12/299,350

(22) PCT Filed: Apr. 30, 2007

(86) PCT No.: PCT/EP2007/054226
§ 371 (c)(1),
(2), (4) Date: Nov. 18, 2008

(87) PCT Pub. No.: WO2007/128737
PCT Pub. Date: Nov. 15, 2007

(65) Prior Publication Data
US 2009/0136988 A1    May 28, 2009

(30) Foreign Application Priority Data

May 4, 2006   (IT) .............................. RM2006A0240
Oct. 24, 2006 (IT) .............................. RM2006A0572

(51) Int. Cl.
*C12N 5/074* (2010.01)
*C12N 5/077* (2010.01)
*C12Q 1/02* (2006.01)
*C12Q 1/24* (2006.01)

(52) U.S. Cl. ............. 435/29; 435/30; 435/366; 435/372

(58) Field of Classification Search .................. None
See application file for complete search history.

(56) References Cited

U.S. PATENT DOCUMENTS 5,486,359 A * 1/1996 Caplan et al. ................ 424/93.7

FOREIGN PATENT DOCUMENTS

EP    1 688 740    8/2006

OTHER PUBLICATIONS

Guglielmi et al. Anal. Chem. 2004, vol. 76, No. 6, pp. 1580-1585.*
Reschiglian et al. "Field flow fractionation and biotechnology". TRENDS in Biotechnology. Sep. 2005, vol. 23, No. 9, pp. 475-483.*
Urbankova et al. Journal of Chromatography B, 1996, vol. 687, No. 2, pp. 449-452.*
Pittenger, M.F. et al., "Multilineage Potential of Adult Human Mesenchymal Stem Cells", Science, vol. 284, No. 5411, pp. 143-147, (Apr. 2, 1999).
Urbankova, E. et al., "Micropreparation of Hemopoietic Stem Cells from the Mouse Bone Marrow Suspension by Gravitational Field-Flow Fractionation", Journal of Chromatography B.: Biomedical Applications, vol. 687, No. 2, pp. 449-452, (Dec. 13, 1996).
Bernard, A. et al., "Red Blood Cell Separations by Gravitational Field-Flow Fractionation: Instrumentation and Applications", TRAC, Trends in Analytical Chemistry, vol. 14, No. 6, pp. 266-273, (Jun. 1995).
Guglielmi L. et al., "Mouse Embryonic Stem Cell Sorting for the Generation of Transgenic Mice by Sedimentation Field-Flow Fractionation", Analytical Chemistry, vol. 76, No. 6, pp. 1580-1585, (Mar. 15, 2004).
Min-Kuang, Liu, "Hydrodynamic Relation in Flow Field-Flow Fractionation using both Split and Frit Inlets", Analytical Chemistry, vol. 63, No. 19, pp. 2115-2122, (Oct. 1, 1991).
Benincasa, Maria-Anna et al., "Cell Sorting by One Gravity SPLITT Fractionation.", Analytical Chemistry, vol. 77, No. 16, pp. 5294-5301, (Aug. 15, 2005).

* cited by examiner

*Primary Examiner* — Vera Afremova
(74) *Attorney, Agent, or Firm* — Nixon & Vanderhye P.C.

(57) ABSTRACT

A method and the relevant instrumentation to fractionate living, adherent stem cells, particularly of human origin, from different sources is disclosed, said method is based on the non-equilibrium, dynamic fractionation of cells assisted by the Earth gravity field.

9 Claims, 6 Drawing Sheets

METHOD AND DEVICE TO FRACTIONATE STEM CELLS

This application is the U.S. national phase of International Application No. PCT/EP2007/054226, filed 30 Apr. 2007, which designated the U.S. and claims priority to Italy Application Nos. RM2006A000240, filed 4 May 2006, and RM2006A000572, filed 24 Oct. 2006, the entire contents of each of which are hereby incorporated by reference.

The present invention relates to the medical field, in particular to a method for fractionation of stem cells and the related apparatus.

BACKGROUND OF THE INVENTION

Stem cells are "primitive" cells devoted to maintain functional and structural integrity of tissues, by replacement of damaged mature cells. Stem cells can be distinguished depending on their different ability to differentiate into different kinds of tissues (different degree of "potency").

Stem cells are distributed in all tissues, and are particularly available from sources like bone marrow, dental pulp, adipose tissue, peripheral blood, umbilical cord and foetal membrane. Stem cells can thus be sorted from such sources, but their localization in each source tissue is not well defined, and cannot be identified in a specific district, isolated from all the cells, more differentiated, which are originated from stem cells.

The low amount of totipotent or multipotent stem cells in human sources different from the embryo requires the use of effective methods of cell sorting/enrichment to make available a sufficient number of stem cells for further applications.

Mesenchimal stem cells, hereafter referred to as MSCs, are adherent, multipotent stem cells that express a panel of surface antigens that is so rich and diversified to limit the possibility to easily distinguish MSCs just on a immuno-phenotypical basis (W. Wagner et al, *Experimental Hematology*, 33 (2005) 1402-1416).

Methods of "negative" selection, which make use of immunomarkers that label non-MSCs, are employed to deplete these "negative" cells from the total cell populations containing also MSCs. Negative selection, however, do not necessarily assure that, among the depleted population of cells that contain MSCs, are no longer present cells which yet are different from the MSCs. Moreover, negative selection allows neither to sort different MSC subpopulations nor to distinguish MSCs from different sources.

Otherwise, "positive" flow-assisted or magnetic-assisted cell sorting (hereafter FACS, and MACS) methods could induce in the sorted MSCs some physiological suffering (i.e. viability reduction), and they could also influence MSC differentiation capabilities, including unpredictable commitment patterns.

Moreover MSCs can be selected by means of a genetic-engineering approach (Gene Transfer Technology, GTT) that require expensive and time-consuming techniques, high investments for personnel-training and genetic manipulation on cells.

It is, then, still an open issue the possibility to sort/select living, adherent, in particular human totipotent or multipotent stem cells such as the MSCs, by means of a method that is relatively simple, inexpensive, which does not effect cell viability and differentiation ability, and which can be applied by bench personnel of standard specialization.

Human MSCs are actually present in different sources, among which bone marrow, amniotic membrane, chorial membrane, Wharton gel, cord blood and placenta, dental pulp, and lipoaspirates. MSCs from different human sources have shown to exhibit different differentiation potential, likely because of the presence of progenitor cells of different types in tissues of different sources (R. Musina et al., *Bulletin of Experimental Biology and Medicine*, 141 (2006), 147-151; C. B. Portmann-Lanz et al., *Am. J. Obstet. Gynecol.*, 194 (2006), 662-663). MSCs isolated from the different sources have shown different level for the expression of the pluripotency marker October 4, evaluated by flow cytometry by means of immunostaining.

In these regards, it is important to focus that, though neither morphological nor phenotypical differences have been observed in the human MSCs obtained from different sources (Musina et al., *Bulletin of Experimental Biology and Medicine*, 139 (2005), 504-509), some preliminary work based on Transmission Electron Microscopy (hereafter referred to as TEM) characterization of the MSCs from different human sources have shown that ultra-structural differences of phenotypically similar MSCs derived from different human tissues can be revelatory of their differences in the in vitro differentiation potential (G. Pasquinelli et al., *Ultra-structural Pathology*, 31 (1) (2006) 23-31).

These findings have supported, in principle, the idea of using a method for sorting human MSCs of different differentiation potential, which exploits the existence of biophysical differences present in the MSC populations.

Field-flow fractionation (hereafter referred to as FFF) methods are able to distinguish morphological and biophysical differences within cellular populations (A. Lucas et al. In "*Field-Flow Fractionation Handbook*"; Schimpf, M. E.; Caldwell, K.; Giddings, J. C., Eds.; Wiley-Interscience: New York, 2000; Chapter 29).

The most classical FFF method using the Earth gravity field (hereafter referred to as GrFFF) is disclosed in U.S. Pat. No. 4,214,982.

The hyperlayer mode is disclosed in U.S. Pat. No. 4,830,756 as particularly suited for the rapid fractionation of ultra-high molecular weight polymer. The effectiveness of the method is explained by the application of an entropic force acting on polymeric chain, with the consequence of the fine settlement of separation, with a precise dependence on molecular weight. A mention to the application of the method neither for cell separation nor for adherent cell sorting is reported in this patent.

In the hyperlayer mode GrFFF is able to fractionate different type of cells, among which winemaking yeast cells in suspension, that is not adherent cells, in order to evaluate cell viability for oenologic applications (patent application ES2239886). The method described in this patent application does not concern the separation and characterization of a specific cell subpopulation, but it only proposes the separation of not-adherent, winemaking yeast cells from non cellular material followed by cell viability determination.

Moreover, GrFFF in the hyperlayer mode has shown to be able to fractionate paucipotent stem cells (hemapoietic) from mouse bone marrow. Nevertheless, they are neither adherent nor stem cells at high potency (Urbánková, E. et al.; *J. Chromatogr. B*, 687 (1996), 449-452). In this work there is no suggestion on the possible employment of GrFFF for the fractionation of cells with morphologic modifications obtained in dynamic conditions; that is that when adherent cells are resuspended they change their conformation, but they reacquire the native conformation with full maintenance of viability once they are back in adhesion.

The inventors have also shown GrFFF as able to fractionate CD34+, human hemapoietic precursor cells, which however are non-adherent cells (12th International Symposium on FFF—Aug. 28-30, 2005; Brno). First indications on the possibility of GrFFF of MSCs from human foetal membrane was also therein given, which however just suggested the possibility to observe qualitative differences between two different samples of MSCs. Neither indications on the possibility to sort the MSCs based on their biophysical differences, nor any evaluation of the so-obtained fractionation recovery and throughput have however been reported.

In fact, GrFFF appears to be unsuitable to high-yield sorting of adherent stem cells such as the MSCs. This is for two fundamental reasons. First, high-through (i.e. preparative-scale) separation methods are know to perform under non-equilibrium conditions. GrFFF in fact develops separation in equilibrium conditions between flow and the applied field. Second, in order to reach such an equilibrium condition necessary to the fractionation mechanism, the GrFFF method requires that, before the flow-assisted fractionation, the cell sample sediments in correspondence of the channel wall of lower gravitational potential (said the "accumulation wall"). This process, said "sample relaxation", requires that the cell sample is injected at a low flow rate regime, and it usually requires also that the injection flow is stopped to make the cell sample sediment at the accumulation wall.

Sample relaxation then is a necessary condition for the GrFFF mechanism. It can however cause cell-cell aggregation/stacking, and possible cell adhesion to the accumulation wall of the fractionation channel.

Therefore, GrFFF should be advised against its use as a high-throughput sorting technique for adherent stem cells, because it performs under equilibrium conditions, and because the achievement of such equilibrium conditions induce possible cell damaging and viability reduction due to cell-cell and cell-channel interaction, which affect their further usage.

A severe prejudice can be then derived against the use of GrFFF as a high-throughput sorting method for the use of adherent stem cells. This prejudice induce a severe conceptual hindrance to the applicability of GrFFF, particularly in the cases of therapeutic applications of human stem cells, for instance in regenerative medicine applications.

Alternatively, it has been shown that it is possible to perform sample relaxation, however for non adherent cells, without any change on flow rate, by means of sample injection directly on accumulation wall.

A combined technique derived from GrFFF, which uses a dielectrophoretic potential (DEP) in combination with the Earth gravity field, is disclosed in WO0196025, and hereafter referred to as GrFFF/DEP. It was applied to sort also adherent cells such as neoplastic cells, but the application to adherent stem cells and the evaluation of possible effects of the DEP on viability and physiology of stem cells have not been reported. Compared to GrFFF, moreover, GrFFF/DEP requires a more complicated instrumentation, and it shows limitations if a scale-up to a high-throughput format is sought, as in the aims of the present invention. This is because also GrFFF/DEP requires the onset of equilibrium conditions between the Earth gravity field and the DEP Due to the more intense field than gravitational field, the FFF variant which employs sedimentation field (SdFFF—Sedimentation Field-Flow Fractionation) is able to perform sample relaxation with reduced interactions with accumulation wall, making it useful also for the fractionation of adherent cells.

The SdFFF in hyperlayer mode has shown to be able to fractionate adherent mouse stem cells lines from cell culture for further applications (Guglielmi, L., et al.; *Anal. Chem.* 76 (2004), 1580-1585). The authors underline that there are critical parameters to be evaluated to obtain the fractionation and enrichment of an enough amount of stem cells for further applications, for the preparation of trans-genic mice and, in particular, with viability maintenance of adherent cells. Some of the authors have already demonstrated that SdFFF operating in the hyperlayer mode is able to separate cells in sterile conditions with fully maintenance of cell viability (Battu S., et al.; *J. Chromatogr. B*, 751 (2001) 131-141).

A properly designed channel for SdFFF, which can be easy disassembled for carrying out easy cleaning and sterilization/decontamination procedures, and which avoids its deformation during usage was proposed to improve fractionation reproducibility of living cells (US 2006/0151403A1). However, with respect to the GrFFF instrumentation, the SdFFF instrumentation setup is intrinsically more complex. High investments for operation and relative instruments do not allow for a disposable use, which is indeed possible with GrFFF, and which is particularly suited in clinical field. Possible online detection of cells, and maintenance of physiological and sterility conditions during fractionation is also more complicated in SdFFF than in GrFFF. Finally, being like GrFFF a method operating in equilibrium conditions, in principle SdFFF is not able to fractionate a number of cells compatible with those needed for direct medical applications (as in transplants).

Although theoretical different from FFF, the split-flow fractionation with a thin capillary channel (SPLITT—Split Flow Thin Cell) is able to give a high throughput sorting of different cells without relaxation, and it suitable for adherent cells. In specific, the gravity-driven SPLITT technique has been shown able to yield a high throughput binary separation in biocompatible conditions of cell populations characterized by pronounced differences in the average dimensions (Benincasa, M. A. et al; *Anal. Chem.*, 77 (2005) 5294-5301). Nevertheless, the SPLITT technique gives only a binary separation into two cell subpopulations, and it is not able to fractionate cells during their elution on a basis of small biophysical differences, both among cells from a heterogeneous population and among cells recovered from different sources. On the other hand, these features are fundamental in order to fractionate stem cells from more differentiated cells present in the same population or to characterize and select stem cell populations recovered from different sources.

SUMMARY OF THE INVENTION

Surprisingly, it has been found that a fundamental and substantial modification of the common GrFFF process removes the above prejudice and the relevant conceptual hindrance. In fact, it satisfies all the requirements to optimally fractionate at high-throughput level adherent stem cells, such as human MSCs, with full maintenance of their viability.

The method of the present invention realizes a flow/gravity-assisted fractionation of the cell sample under non-equilibrium conditions. Under these conditions, no relaxation occurs, which indeed is a fundamental requisite to reach the requires equilibrium conditions in GrFFF of cells.

Since the flow-assisted fractionation process requires cells being in suspension, the method of the present invention in fact realizes cell fractionation based on the cell biophysical differences acquired in dynamic conditions. This means that during fractionation the cells are in suspension and, then, they acquire features that may be different from the features of their native, adherent state. The differences in cell features that are dynamically acquired during fractionation allow for cell fractionation in a flow-assisted, suspended state. Because of the extremely gentle fractionation conditions, native cell features are fully restored when cells return to the adherent state after fractionation completion, and cell viability is fully preserved.

Moreover, one of the major advantages brought about by the present invention is the possibility to isolate cell fractions with unequal differentiation potential correlated to different hierarchical level of stemness, which can be used to improve application of stem cells in biomedical fields.

The method of the present invention is then based on a principle that is conceptually new, and which cannot be obviously deducted from the common GrFFF mechanism. GrFFF would, in fact, require conditions that are not suited to optimally fractionate at a high-throughput scale adherent stem cells like, for example, the MSCs.

The method of the present invention will be hereafter referred to as Non-Equilibrium, Earth Gravity-Assisted Dynamic Fractionation (NEEGA-DF).

The present invention shows the unexpected advantages of low investments, operations and maintenance costs for the instrumentation, that can be sterilized by means of an autoclave or potentially used in disposable formats.

The present invention gives a method for the high throughput fractionation of viable, totipotent stem cells, in particularly human stem cells, with important biomedical consequences, such as safer and more probable transplants.

Since it is not necessary to control cell-cell or cell-device interaction during fractionation, the NEEGA-DF method is suited to employ any transport fluid (hereafter referred to as mobile phase). In particular, the cell culture medium can be employed as mobile phase. This ensures optimal physiological conditions of the cells during the fractionation process, which favours full maintenance of cell viability and the highest cell recovery after fractionation.

The fractionated cells can be further characterized and/or sorted using either the same method provided by the invention (through the same system or through same, coupled systems) or a panel of immuno-markers which can be different or simplified in number with respect to the panel that would be necessary to sort the cells if they were not previously fractionated.

Otherwise, the fractionated cells can be just immediately employed, or stored for further usage. That is, after fractionation the cells are collected and transferred on proper surfaces to favour the re-adhesion process that is necessary to obtain their in vitro expansion before any further usage. The fractionated, possibly expanded cells can, for instance, be committed to a specific differentiation pattern able to induce a cell phenotype that is required for in vivo applications in different fields, for instance in regenerative medicine.

The method and instrumentation provided by the invention guarantee full biocompatibility and maintenance of cell viability for further cell growth and/or in vitro expansion towards in vivo applications. Because of its technical characteristics, the instrumentation can be easily sterilized before usage. It can be also realized in disposable format, which makes it extremely convenient for clinical applications.

Because of the absence of cell relaxation, the NEEGA-DF method is intrinsically suited to give high sample recovery and, despite FFF techniques, being a non-equilibrium fractionation method it fundamentally suitable to increase the fractionated cell throughput.

In summary, it is an object of the present invention a method for the high-throughput fractionation and further use of adherent stem cells, particularly human, totipotent or mul tipotent stem cells such as the MSCs, isolated from different sources. Said method comprises the following steps:

a) preparation of a living cell sample suspended in a biocompatible fluid used as mobile phase;
b) introduction of said sample into a proper device for non-equilibrium, gravity-assisted dynamic fractionation (NEEGA-DF), said introduction performed by means of a continuous flow of mobile phase applied in a direction that is coincident with the direction of the gravity field;
c) sample elution from said fractionation device;
d) collection of fractions containing said fractionated stem cells.

In addition, following step d), the method provided by the invention may include a further step of isolation of the fractionated cells, as well as their possible further characterization/selection and/or in vitro expansion.

The present invention also provides the use of a proper device to carry out the above described method, as well as the optimised devices that can be used for the execution of the method.

The invention can be applied to totipotent stem cells and to their extended stem cell descendants, including multipotent and paucipotent stem cells.

The present invention also relates to stem cells obtainable by the above method.

In particular, stem cells obtainable as above are adult stem cells of human origin, for example MSCs.

Adult stem cells according to the present invention can be sorted from bone marrow, dental pulp, adipose tissue, peripheral blood, placenta, umbilical cord and foetal membrane, amniotic membrane, chorial membrane, Wharton gel, and lipoaspirates.

Depending on the applicable law, certain Countries do not allow manipulation of embryonic stem cells. As far as this restriction affects the scope of the claims of the present invention is concerned, it is intended that subject-matter forbidden by virtue of law is disclaimed.

Compared to currently available cell sorting methods solely based on immuno-labelling or gene selection technologies, the method provided by the invention overcomes or, at least, reduces the issues related to the difficult individuation of the immunomarker panel, to the possible influence of the immuno-labelling process on viability and differentiation capabilities of the sorted cells, and to the influence of genetic modifications on the cell population. Instrument investment and maintenance costs, as well as method development and bench personnel training costs are also drastically reduced.

With respect to the common FFF-based cell sorting methods, the method of the present invention overcomes limitations due to biocompatibility and sterility issues, to compatibility with adherent cells, and to a relatively low sample recovery and throughput.

Most generally, the investment, maintenance, application and training costs are most favourably reduced.

DEFINITIONS

For Totipotent Stem Cells it is meant cells able to differentiate into all mature tissues of the organism.

For Multipotent Stem Cells it is meant cells which can develop into mature tissue types belonging to a definite embryonic germ layer (Endoderm or Mesoderm or Ectoderm).

For Mesenchymal Cells it is meant cells which derive from Mesoderm, which can develop into the embrionic connective tissue, also known as Mesenchyme.

Mesenchymal Cells are adherent cells, where adherent it is meant that their isolation from the other cells forming the whole sample and that their ante- or post-fractionation in vitro growth occurs through adhesion on specific containers employed for isolating and culturing cells.

For Biocompatibility it is meant the fully maintenance of cellular physiology, included viability, when cells pass from adhesion to suspension conditions, and viceversa.

For Suspension it is meant the cell detachment from plastic surface used for culturing cells for their homogeneous dispersion in a fluid.

For Non-native Biophysical Properties it is meant the properties, included the morphological and dimensional features, that cells assume during dynamic conditions when they are suspended in the transport flow.

For Fluid it is meant the fractionation fluid or a different fluid used to prepare cell suspension after their detachment, able to preserve cell viability in suspension.

For Injection it is meant the introduction into the fractionation element of a proper amount of suspended cells.

For Proper Amount of cells it is meant the minimum amount of cells that, after the fractionation process, yields a number of cells in each fraction useful for further cell culturing or direct applications.

For Fractionation it is meant separation of the different cellular components suspended in mobile phase on the basis of biophysical differences.

For Detection it is meant the identification and quantification of cells after their fractionation, that is at the outlet of fractionation device, both within and externally to it. For within it is meant that cells can be detected without any contact with devices different or external to the fractionation device.

For Cell Collection it is meant the deposition of aliquots of mobile phase containing different subpopulation of fractionated suspended cells, in order to restore cell adhesion conditions.

For Mobile Phase it is meant a physiologic buffer solution, optionally added with antibiotic, indicators, nutrients and inerters, which is employed for the injection, fractionation and cell collection after fractionation.

For Antibiotic it is meant a substance able to maintain cell sterility and viability.

The Indicator is defined as a substance able to visualize the maintenance of biocompatibility conditions.

For Nutrients it is meant substances able to maintain cells viable and to allow their growth in adhesion conditions, after the fractionation process.

For Inerters it is meant factors able to enhance surface chemical inertia of the fractionation device.

DETAILED DESCRIPTION OF THE INVENTION

The invention will be hereafter disclosed in detail also by means of examples, as well as by drawings in which.

The method according to the present invention is based on the possibility to discriminate different cell subpopulations that have differences in their non-native biophysical features, said differences being dynamically achieved when cells are suspended in the mobile phase. As "non-native biophysical features" are considered the cell morphological features that can result to be different from the features that cells own during their natural, in vitro growth and reproductive cycle as adherent cells. For "dynamic conditions" it is meant that the biophysical features are acquired by the cells when they are placed in suspension in a fluidic regime.

As already mentioned above, this feature of the method of the present invention provides a remarkable advantage, making available selected fractions of stem cells with diverse and higher differentiation capability with respect to the starting populations of cells, that is before that the fractionation method of the present invention is carried out.

A characteristic aspect of the method provided by the invention is that the flow-assisted sample fractionation occurs in non-equilibrium conditions.

For "non-equilibrium" it is meant that the mobile phase flow is neither modified nor stopped after the sample injection and before the fractionation process. As a consequence, once the sample has been injected into the NEEGA-DF device, and before the fractionation process, the cell sample does not sediment at the accumulation wall, and during fractionation the cells are swept down the fractionation channel at a given distance from the wall.

The lack of sample sedimentation to reach the equilibrium conditions before sample fractionation, this process said "sample relaxation", avoids the onset of what would be in fact observed if the common GrFFF technique were used. That is, NEEGA-DF avoids the natural tendency to adhere to the accumulation walls that adherent cells would display if fractionation would be performed according to the GrFFF process. Cell adhesion would in fact inhibit the ability of the adherent cells to maintain their suspension conditions and their biophysical features acquired in dynamic conditions, as well fractionated cell recovery. Stacking/aggregation of different subpopulations of the adherent cells would also jeopardize the sorting capability of the method.

The lack of sample relaxation also inhibits the establishment of the equilibrium condition between the gravitational field and the counteracting, flow-induced lift forces acting on the cells. Said equilibrium condition is necessary to the establishment of the hyperlayer mechanism on which the common GrFFF process of cells is based.

It follows that the NEEGA-DF mechanism provided by the invention altogether results to be defined as a dynamic, non-equilibrium process. Non-equilibrium conditions are proper of separation methods scaled up to high-throughput (i.e. preparative scale) applications, which is not in fact the case of the common GrFFF method.

All the above aspect confers to the NEEGA-DF mechanism the following features, which clearly distinguish NEEGA-DF from the common GrFFF mechanism:
- absence of any possible contact between sample cells and the fractionation device
- maintenance in dynamic conditions of the differences in the non-native biophysical features of the cells. This is due to the fact that the adherent cells are maintained in suspension from before the injection process to the end of the NEEGA-DF process;
- possibility of high-throughput cell fractionation.

In a first, preferred embodiment the invention is applied to the fractionation of MSCs, in particular human MSCs, which are isolated from bone marrow, amniotic membrane, chorial membrane, Wharton gel, cord blood and placenta, dental pulp, and lipoaspirates.

The method provided by the invention can be also applied to the in vitro or in vivo amplification of the fractionated cells, and to the enrichment of stem cells from different ex vivo or ex vitro sources in order to enhance their ability to differentiate into different specialized cells.

The fractionated cells provided by the invention can be employed to enhance the implementation of biomedical, clinical and biotechnological applications such as autologous or heterologous transplantations, organs regeneration, creation of bionic organs, and to the therapy of neoplasiae in different fields, e.g. in dermatology, vascular surgery, cardiology, haematology, and gastroenterology. As above described, the invention provides a method for fractionating living, adherent, particularly human, totipotent stem cells and their extended descendants, including multipotent and paucipotent stem cells, in particular multipotent MSCs from in vitro cell cultures that are obtained by isolation of the cells from the organism sources in which they are present.

The cells are suspended in a proper manner, and injected into a properly designed NEEGA-DF system. The cells are injected into the fractionation device by means of a continuous flow of biocompatible mobile phase. The flow is never stopped, and the flow rate is set at a value for which the cells do not sediment at the wall of the fractionation device which is located oppositely to the direction of application of the gravity field. The chosen flow rate also avoids that, during fractionation, the cells come in contact with the fractionation channel walls, being cells swept down the fractionation channel at a given distance from the channel walls. The heterogeneous cell sample is fractionated in different, more homogeneous subpopulations, said fractionation based only on differences in the biophysical features of the cells. At the fractionation device outlet, a detection system is connected to detect the fractionated cells, when necessary. A fraction collector is connected downstream the detector outlet. The complete instrumentation for the execution of the method provided by the invention basically comprises:
- a cell injection device,
- at least one fractionation element,
- at least one fluid reservoir,
- at least one vessel for the fraction collection,
- at least one flow generating device, and optionally
- a detector.

Most conveniently, the whole method is carried out in a sterile environment. The system is placed, for instance, in a class II, laminar-flow hood.

A data acquisition system may be either externally placed or built in the instrumentation. In the latter case, a remote control for the data acquisition process is necessary.

For the application of the NEEGA-DF procedure, the system provided by the invention may be similar, in some aspects, to the conventional GrFFF system as disclosed in U.S. Pat. No. 4,214,981 or in patent application ES 2239886. Substantially, the fractionation device that is necessary to the application of the method provided by the invention is constituted of two parallel plates that are separated by a spacer from which the channel volume is removed.

The ensemble constituted of the two plates and the spacer may be welded or rather sandwiched together using proper clamping systems, which can be, in case, removable clamping systems such as nuts, bolts or rivets.

In the case of welding or fixed clamping systems, the device results to be particularly suited to a disposable usage. In the case of removable clamping systems, the device can be easily disassembled for cleaning, sterility and maintenance procedures.

The channel has at least one inlet and one outlet, respectively constituted of one hole drilled in one or both the bars. The inlet hole has the diameter that is necessary to the connection of the channel with the sample injection device. The outlet hole size must allow for a low-volume connection with the detector and/or the fraction collector.

In the most general invention embodiment, the fractionation device can be constituted of fractionation channels of different shape and, most conveniently, it is mounted using removable clamping systems.

Figure 1:
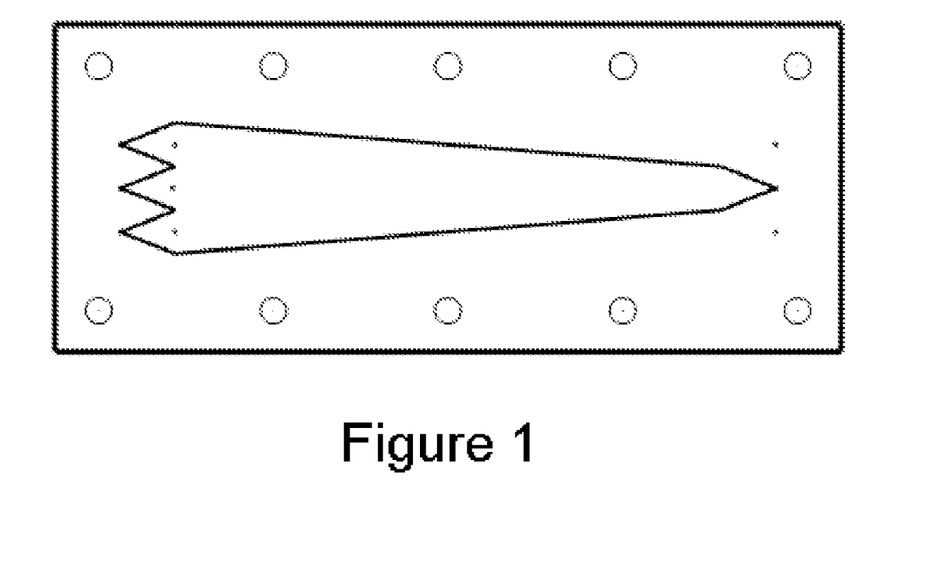
FIG. 1 shows a first realization of the fractionation channel provided by the invention.
Figure 2A:
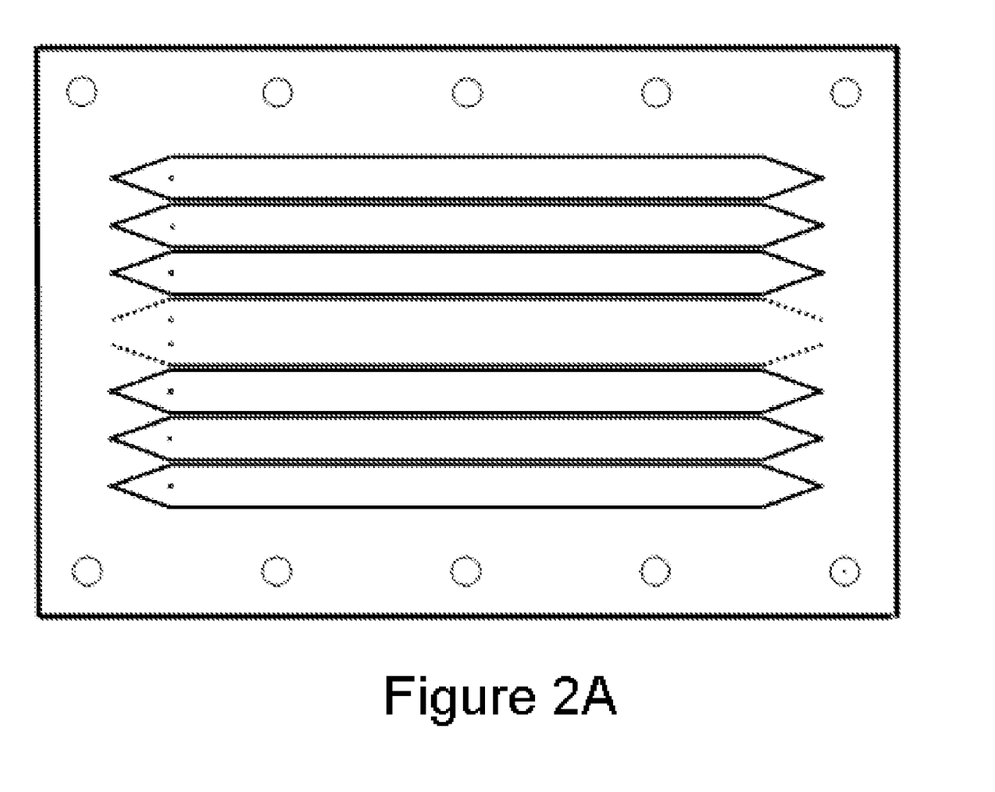
FIGS. 2A, and 2B show other realizations of the fractionation channel provided by the invention.
Figure 2B:
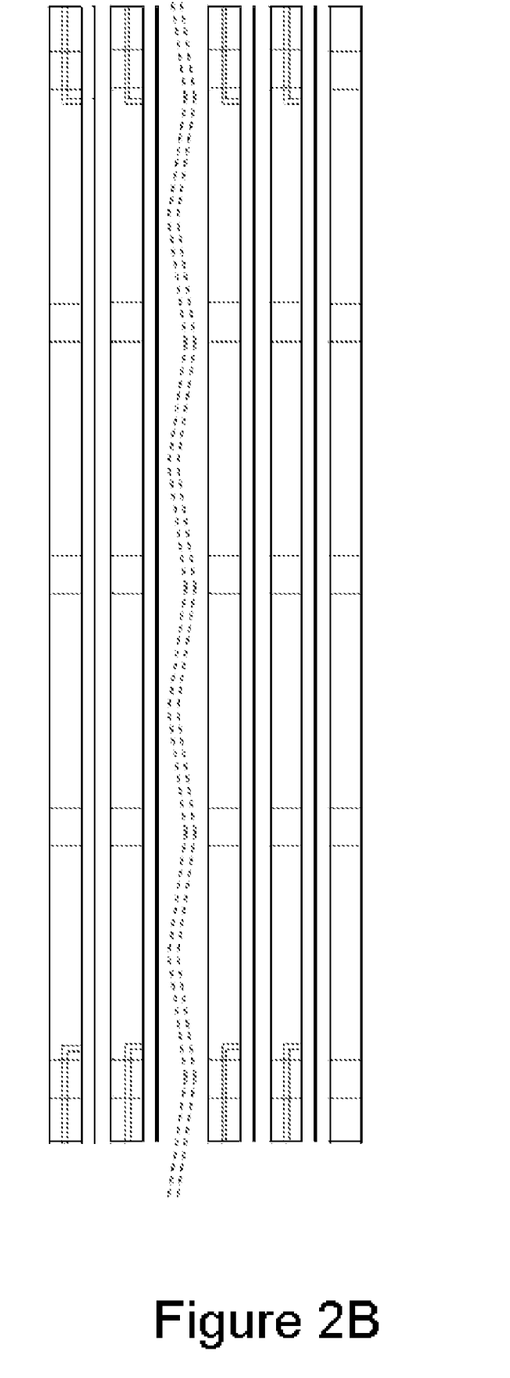

To enhance the fractionated cell throughput, the invention provides a system embodiment that employs new channels, as those depicted in FIGS. 1, 2. In a first embodiment, the new channel presents the two longest edges that converge towards the downstream direction, and a multiple-V shaped front side (3 in the exemplifying drawing) with the concavity lying towards the flow direction.

At the end of the multiple-V-shaped area, the two longest edges of the flow channel converge until they join together with the rear side end where the channel outlet hole is placed. The side end is characterized also by a V-shaped area with the concavity that lies against the direction of the V-shaped front side. An inlet hole for sample and flow injection can be placed in each V-shaped area of multiple initial section. Alternatively the inlet hole for cells injection can be placed at the basis of the three initial V-portion (as shown in FIG. 1) allowing for multiple and separate injection of cells and mobile phase.

In another embodiment the device results to be composed of three channels (3 in the exemplifying drawing). Two devices can be combined as two parallel sets, as shown in FIG. 2A, or piled up, as shown in FIG. 2B. Each channel has V-shaped ends. The concavity of the front side end lies towards the flow direction, while the concavity of the rear side end lies against the flow direction. In the terminal section of the V-shaped areas at the front and at the rear side ends are drilled, respectively, the sample injection hole and the sample outlet hole. Alternatively, the inlet holes for cells injection can be placed at the basis of each initial V-shaped area allowing for multiple and separate injection of cells and mobile phase. This embodiment is suitable for high throughput applications (High-Throughput NEEGA-DF, HT/NEEGA-DF), where for high throughput applications it is meant that the system can be applied for the fractionation of sample containing from one to several millions of cells respectively.

In a preferred embodiment of the invention, the single separation device is a flat capillary channel that is 20-30 cm long, 1-2 cm wide and 100-300 μm thick. The capillary is obtained from a plastic sheet of proper thickness, hereafter referred to as the "spacer". Said spacer is sandwiched between two mirror-polished plates, hereafter referred to as channel "walls". The so-obtained channel is sealed to prevent fluid leakage. Channel walls are outfitted with a capillary tube for the carrier liquid inlet, which is connected to the cell injection valve, and with a capillary tube for the cells and carrier liquid outlet. The channel is held in a horizontal position to make the gravitational field act perpendicularly to the carrier liquid flow.

In another, particularly preferred embodiment of the invention, the whole fractionation device is made of thermoresistant, biocompatible plastic material that is suitable for sterilization by autoclave or by other methods, for instance by high-energy irradiation (e.g. ultraviolet or gamma rays).

In a particular embodiment of the invention, the fractionation device is made of biocompatible plastic material suited to realize disposable medical devices.

Plastic materials that are sterilizable by different protocols, and which are suited to the construction of the fractionation device are, for instance: polyvinyl chloride (PVC), polycarbonate (PC), polystyrene (PS), polypropylene (PP), polyethylene terephthalate (PET), and polybutylene terephthalate (PBT).

Most conveniently, the chosen plastic material is transparent, which allows for the in situ detection of the eluted cells at the channel outlet by means of image acquisition systems.

A possible way to realize a multi-channel device is illustrated in FIG. 2A and FIG. 2B.

The NEEGA-DF system is constituted of: a pumping system for the mobile phase flow generation, for sample injection, and for channel cleanup; a fluid reservoir for the storage and delivery of fluids, including the mobile phase, and for the cleaning and decontamination fluids for the fractionation system; an injection system to introduce the sample in the capillary channel; sample collection systems at the channel outlet; detection and data treatment systems.

The pumping system can be of conventional type, for instance of the type used in the instrumentation for flow-assisted analytical techniques such as liquid chromatography or flow-injection analysis. The injection system includes conventional valves, which are available, for instance, from the manufacturer Rheodyne Inc., and which are combined with the above-mentioned pumping system.

The detection system comprises different possibilities that are conventionally used in flow-assisted analytical techniques such as liquid chromatography or flow-injection analysis, or in cell analysis instrumentation. Among these, UV/vis spectrophotometers, fluorescence detectors, luminometers, flow cytometers and microscopy systems are particularly useful.

Process fluids, particularly the mobile phases, must be biocompatibile to guarantee cell sterility, integrity, and viability. Possible mobile phases are, for instance, physiological buffered saline solutions (like the Phosphate-Buffered Saline solution, hereafter referred to as PBS, at pH=7.4), culture media used for the cell growth (like, for instance, MEM, DME, IMDM from the manufacturers Life Science Research or Sigma-Aldrich), or their modifications.

Stem cells are isolated following known procedures depending on the cellular sources (bone marrow, foetal membranes, dental pulp), and they are selected exploiting their property to adhere to culture flasks.

Cells are maintained in culture with an appropriate medium, for example in a 6-wells plate until they reach sub-confluence.

Once the cells reached sub-confluence, they are expanded with an enzymatic treatment for cell detachment from plastic surfaces.

The expanded, adherent cell population with a fibroblast-like morphology is then characterized to verify the presence of a selected number of typical mesenchymal markers, and the absence of haemopoietic markers that can be related to the presence of contaminant cells.

The characterization is performed by flow cytometry or other proper technique.

After cells are recovered from the wells, they are suspended in a suitable culture medium in order to be injected into the NEEGA-DF. For example, for human MSCs, the DMEM (Dulbecco's Modified Eagle Medium) with 10% FBS (Fetal Bovine Serum) supplemented with penicillin and streptomycin, or analogous substances, can be used.

To perform the method according to the present invention, the device has to be conditioned with proper procedures that are common to the normal laboratory practice.

For the employment of cells after the fractionation process, all the NEEGA-DF instrumentation has to be properly sterilized. Then the system is conditioned for a suitable time, for example 30 minutes before starting the fractionation, using a high flow rate of the same sterile mobile phase used for the cell fractionation.

Just before the injection, cells have to be properly maintained in suspension to avoid cell aggregation. The cell suspension (conventionally, 45 µl in volume) is injected by means of an injection valve. According to the NEEGA-DF principle, cell fractionation is performed at the same mobile phase flow rate used for the cell sample injection, which typically is of 0.45 ml/min. These flow conditions also allow for the cells being eluted at a certain distance from the fractionation channel walls. This distance is never lower than the average cell size. In order to generate the necessary mobile phase flow inside the NEEGA-DF channel, a peristaltic pump (GILSON Miniplus 3) is usually employed.

During the NEEGA-DF process, eluted cells are collected at different elution times as different fractions in sterile vials.

Development of the cell NEEGA-DF process is monitored by means of a detection system, which conventionally is an UV/vis spectrophotometer equipped with a flow-through cell, with the signal acquired at a defined wavelength, conventionally 600 nm.

Cells collected in each fraction can be characterized and kept for further applications, or they can be immediately employed.

The following examples further illustrate the invention, wherein the achievement of a surprisingly effective fractionation of viable, human MSCs having different differentiation potential is provided.

EXAMPLE

MSC Sample Preparation and Characterization

Isolation of MSC Populations
Preparation of the Cell Samples Generally Follows Procedures that do not Require further explanation with respect to the common knowledge of a person of ordinary skill in the art.

MSCs are isolated by means of specific methods depending on the different sources of cells, and they are selected exploiting their property to adhere to culture flasks.

Cells are cultured in the suitable culture medium DMEM (Dulbecco's modified Eagle Medium) with 10% FBS, and supplemented with 100 U/ml penicillin and 100 µM streptomycin. Then they are incubated at 37° C. with 5% $CO_2$. Culture medium is replaced two or three times per week.

Once the cells have reached sub-confluence, they are expanded with an enzymatic treatment for cell detachment from plastic surfaces. Cells are then washed twice with PBS, and incubated for 3 minutes at 37° C. with a 0.25% trypsin-EDTA solution with 5% $CO_2$. Trypsin activity is neutralized by addition of DMEM with 10% FBS, and the resulting cell suspension is centrifuged at 1,000 rpm for 5 minutes. The final cell pellet is resuspended in fresh culture medium, and then it is seeded in a triple growth surface. Viable cell counting is performed in a Neubauer chamber by staining the cells with the vital dye Trypan blue.

The expanded, adherent cell population with a fibroblast-like morphology is then characterized to verify the presence of a selected number of typical mesenchymal markers, and the absence of haemapoietic markers that can be related to the presence of contaminant cells. The characterization is performed by flow cytometry.

Cells are stained with the following anti-human antibodies: SH2, SH3, SH4, anti-CD 166, anti-CD29, anti-CD14, anti-CD34, anti-CD45, conjugated with the fluorescein isothiocyanate (FITC) fluorochrome.

The immunophenotypic characterization protocol for each assay employs about 100,000 cells placed into specific vials for cytometric analysis and, subsequently, their incubation with the conjugated monoclonal antibody for 15 minutes at room temperature in the dark. Cells are then centrifuged for 8 minutes at 1,000 rpm. The supernatant is removed by pipetting, and it is discarded. Cell pellet is washed twice with PBS, and finally cells are resuspended in PBS for cytometric analysis. For each antibody tested, 10,000 events are acquired with a throughput rate of 100-150 events/s.

NEEGA-DF of MSCS

System Setup and Sample Handling

Before the NEEGA-DF process, all the NEEGA-DF instrumentation is properly sterilized and, then, placed into a laminar flow hood. Then the system is conditioned for 30 minutes using of a high flow rate of sterile mobile phase. The mobile phase is composed of PBS supplemented with 0.1% BSA and 1% antibiotic. It is usually stored at 4° C., and it is allowed to reach room temperature before use.

As described above, cells are seeded in 6-well plates, and maintained in culture medium (DMEM 10% FBS) until they reach sub-confluence. Cells are then recovered from the wells, and injected into the NEEGA-DF system.

Each well is washed twice with PBS and, then, treated with a 0.25% trypsin-EDTA solution following the above-described protocol. Cells are then centrifuged at 1,000 rpm for 5 minutes, and resuspended in DMEM culture medium. The first well content is usually employed for cell counting, from which it is determined the actual volume in which the cells are resuspended in all the other wells. This is made if it is considered that the volume injected into the NEEGA-DF system is 45 µl, and the number of injected cells ranges from 100,000 to some millions.

NEEGA-DF of the Cell Population

From each well, cells are suspended in the culture medium DMEM. Before the injection, cells are properly maintained in suspension to avoid cell aggregation. The cell suspension (conventionally 45 µl in volume) is injected by means of an injection valve.

According to the NEEGA-DF principle, cell fractionation is performed at the same mobile phase flow rate used for the cell sample injection, which typically is 0.45 ml/min. These flow conditions also allow for the cells being eluted at a certain distance from the fractionation channel walls. This distance is never lower than the average cell size. In order to generate the necessary mobile phase flow inside the NEEGA-DF channel, a peristaltic pump (GILSON Miniplus 3) is usually employed.

During the NEEGA-DF process, eluted cells are collected at different elution times as different fractions in sterile vials.

Because of the high reproducibility of the NEEGA-DF process, to increase the number of cells in each fraction, repeated collections of cells (collected at the same elution time intervals) can be accumulated. This is performed by maintaining the collecting vials in ice bath. However, collected cells cannot be maintained in suspension for more than two hours to avoid cell suffering.

Figure 3:
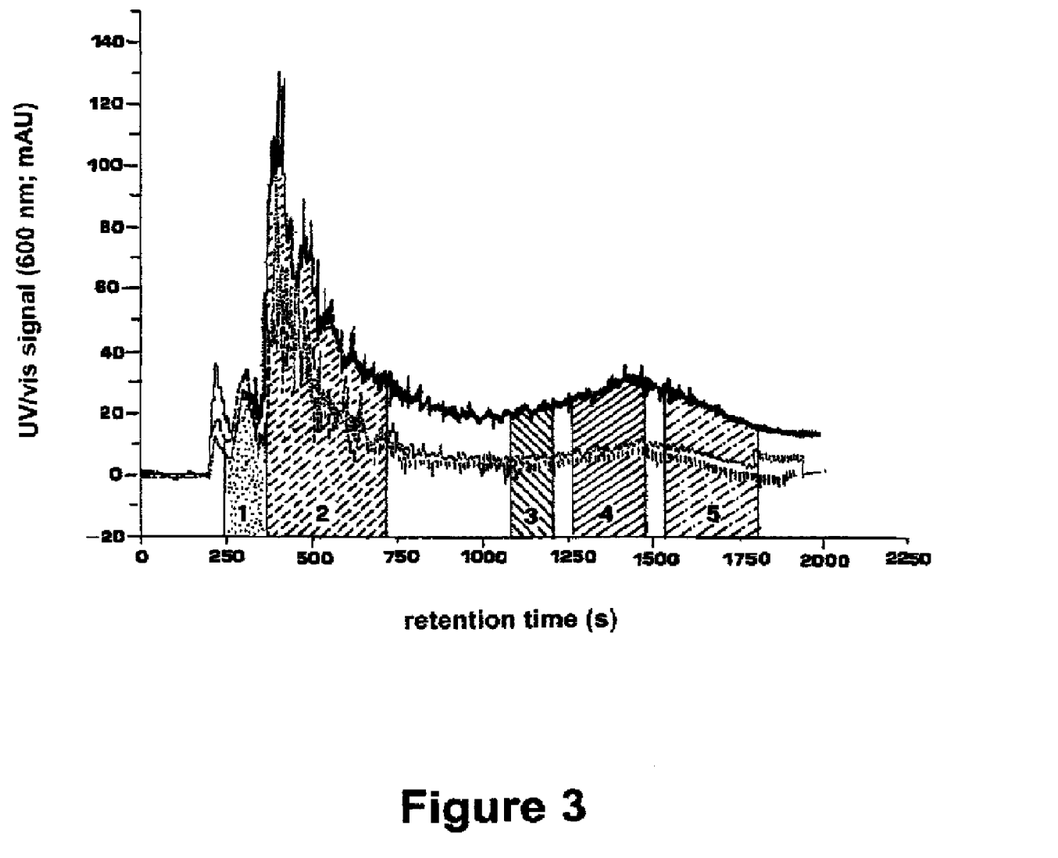
FIG. 3 shows an example of MSC fractionation provided by the invention; MSCs were obtained from human fetal membrane. Three repeated runs are superimposed, and the time intervals for collection of the five fractions analysed in FIG. 4 are indicated.

Development of the NEEGA-DF process is monitored by means of a detection system, which conventionally is a UV/vis spectrophotometer equipped with a flow-through cell. Cell elution from the NEEGA-DF channel generates a signal at a defined wavelength, conventionally 600 nm, which can be acquired and recorded. In FIG. 3, the fractionation results obtained in three repeated NEEGA-DF runs of MSCs from human foetal membrane is shown. The indication of five fraction collection is also therein reported.

Figure 5:
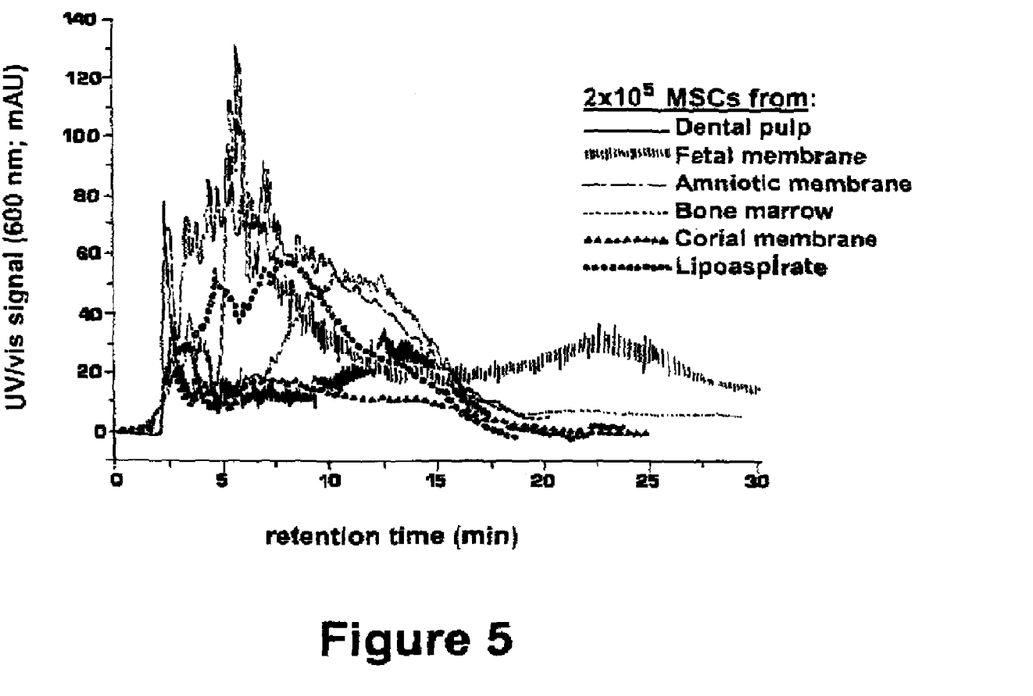
FIG. 5 shows differences in the fractograms obtained for MSCs isolated from different human sources. The observed differences in the fractograms reflect differences in the biophysical features of the MSCs originated from different sources.

Different MSC populations obtained from different human sources display clear differences between the relevant fractograms. In FIG. 5 the different fractograms obtained for approximately 200,000 MSCs from, respectively, bone marrow, amniotic membrane, corial membrane, foetal membrane, dental pulp and lipoaspirate are superimposed. According to the NEEGA-DF process, the observed differences in the fractograms of MSCs obtained from different sources reflect differences in their biophysical features. These findings may be revelatory of differences in the differentiation potential of MSCs from source to source.

Characterization and Differentiation of the Fractionated Cells

Cell recovered from each fraction are centrifuged at 1,000 rpm for 5 minutes. They are then resuspended and maintained in suspension under proper conditions that depend on further needs or uses of the cells, i.e. for cellular seeding and amplification for cell reuse, or for further cell cytofluorimetric characterization and/or immuno-based, post-fractionation sorting, or for commitment to specialized cells (i.e differentiation).

Following a protocol similar to the protocol above employed for the pre-fractionation cell characterization, or other known protocols for cell immunolabeling, post-fractionation sorting can use a panel of selected immunomarkers that can be different either in type or in number with respect to the panel that should be employed if cells were not fractionated.

Figure 4:
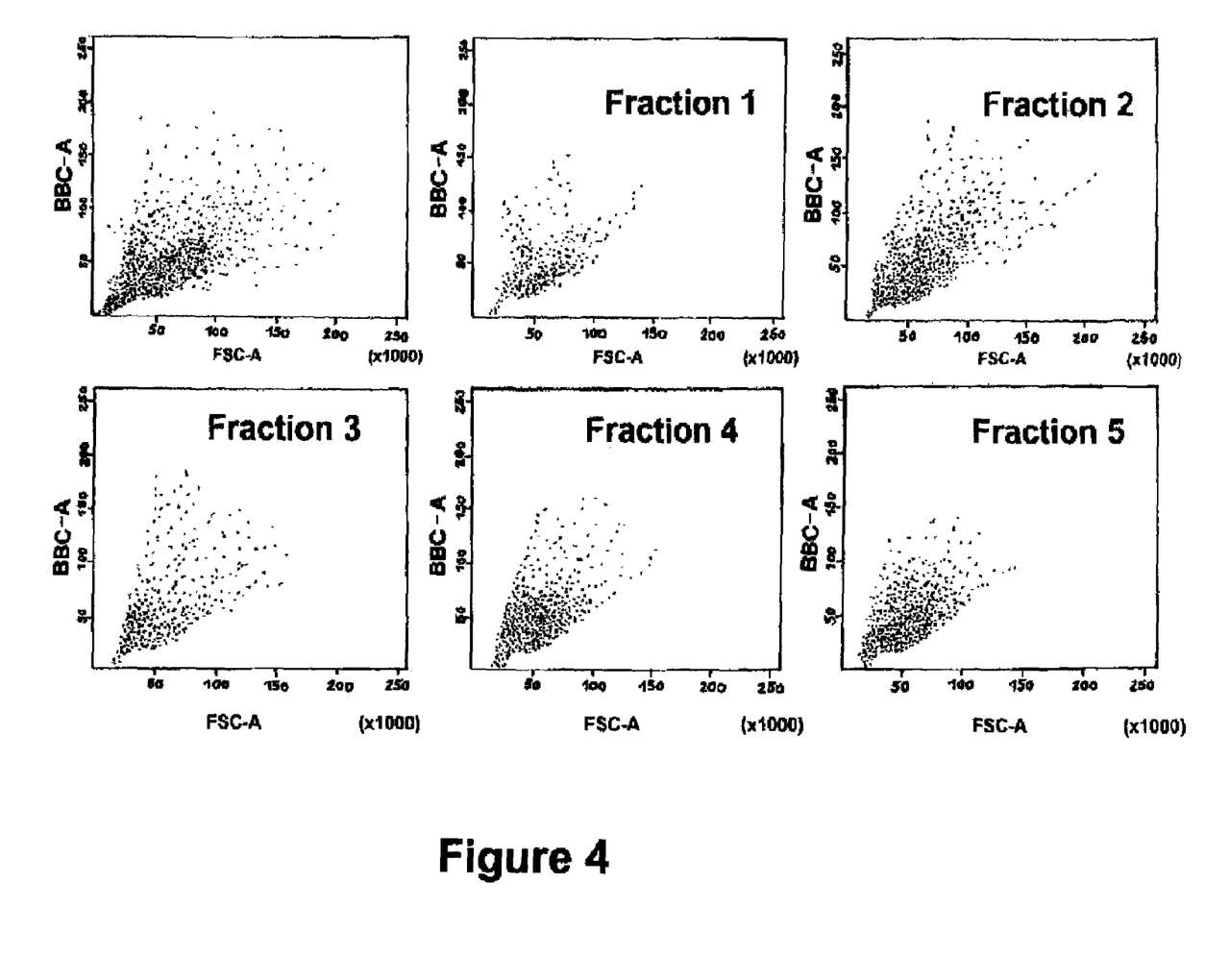
FIG. 4 shows an example of stem cell fractionation provided by the invention, as well as the results of cytometric analysis (forward scatter signal vs. side scatter signal) performed on the cell fractions. Cytometric analysis indicates differences in the biophysical features of the cells within different stem cell fractions.
Figure 6:
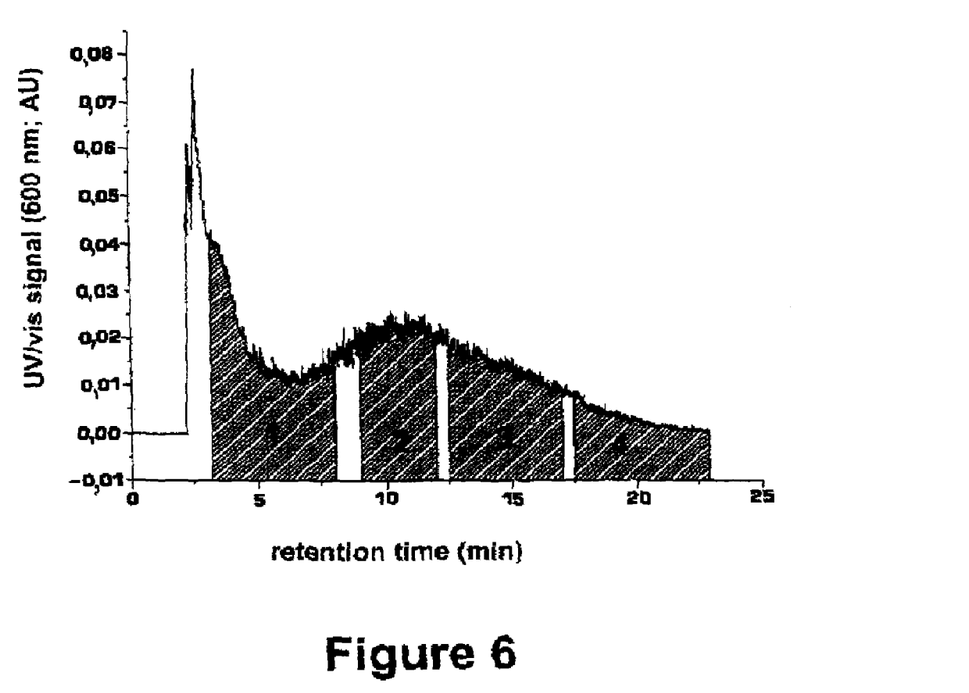
FIG. 6 shows a fractogram obtained for MSCs isolated from human dental pulp. More retained fractions show lower standard deviation values (i.e. higher homogeneity) of cell area, as determined by high-resolution optical microscopy.

A number of fractionated cells, usually in the range of 50,000-100,000 for each fraction, are suspended in a volume of PBS, which typically is 0.5 ml. By cytometric analysis, the presence of differences in morphology/biophysical features between cell subpopulations analyzed under dynamic conditions in fluid suspension can be ascertained. This is performed by mapping the forward scatter (FS) and the side scatter (SS) signals originated from cell samples from the different fractions. Differences in the FS/SS maps can be found, as shown in FIG. 4 that reports results for the fractions of MSCs from human foetal membrane represented in FIG. 3. It can be observed that cells present in the more retained fractions (e.g. in the Fraction 5) are, in morphology, more homogeneous than cells present in the less retained fractions (e.g. in the Fraction 2). Morphological analysis performed by high-resolution optical microscopy confirms these indications. In FIG. 6 it is reported the fractogram obtained for a sample of MSCs obtained from human dental pulp with the standard deviation values of the fractionated cell area values determined for the fractions: the higher cell retention, the higher homogeneity of cell morphology. All these findings also demonstrate that cell fractionation is actually based on differences in cell morphology/biophysical features when cells are suspended in a fluid regime.

An aliquot of cells recovered from each fraction are also suspended in DMEM with 10% FBS, and placed in a 6-wells plate. The cells are then placed in the incubator for at least 24 hours to allow them to adhere to the flask plastic surface and to reestablish their adherent, native morphology. Microscopy is then performed to verify cells adhesion, viability, and the absence of contaminant microorganisms. Subsequently, each fraction is induced towards a specific differentiation pattern using specific induction media.

For the osteogenic differentiation, for instance, the proper culture medium purchased from Stem Cell Technology Inc. is employed following the protocol furnished by the manufacturer: MesenCult Basal Medium, 15% Osteogenic Stimulatory supplement (human), 0.5 µM ascorbic acid, 0.1 µM dexamehtasone, 10 mM 13-glycerophosphate. The induction proceeds for 2 weeks by changing fresh culture medium every 3 days. Cells are then fixed with 10% formalin, and stored at 4° C. Osteogenic differentiation is assessed by von Kossa's staining for determining the presence of mineral calcium deposition.

For the adipogenic differentiation, the induction protocol consists of alternate medium changes with "Induction" and "Maintenance" media. "Induction" medium consists of: DMEM supplemented with 10% FBS, 0.5 mM isobutyl-methyl xanthine (IBMX), 200 µM indomethacin, 1 µM dexamethasone and 10 µg/mL insulin (all from Sigma). "Maintenance" medium consists of: DMEM supplemented with 10% FBS and 10 µg/mL (Sigma). After 3 weeks of culture the cells contained neutral lipids drops in the cytoplasm, visible by optical microscopy analysis, were stained with Oil Red O solution for determining the presence of the fat vacuoles.

Figure 7:
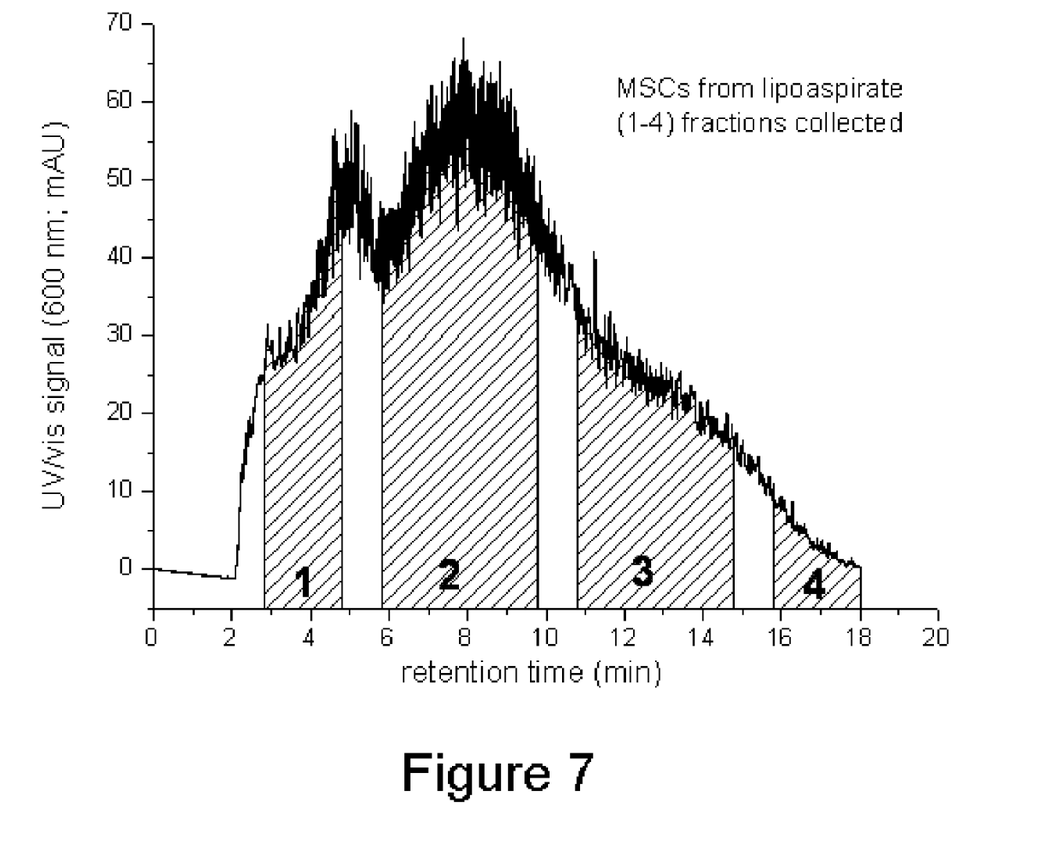
FIG. 7 shows the fractogram obtained for MSCs isolated from human adipose tissue and the time intervals for collection of the four fractions that underwent to differentiation to adipocytes.

Adipogenic differentiation was performed on cells collected from the NEEGA-DF fractionation of MSCs isolated from adipose tissue. The relevant fractogram obtained following the protocol above described is reported in FIG. 7, where the four collected fraction are shown. Cells collected from each fraction were seeded in the proper tissue-culture plates at a density of $17 \times 10^3$ cells/cm$^2$, and the induction proceeds for 3 weeks with changes of culture medium every 3 days.

The results indicate that cells with the higher adipogenic differentiation capability (with respect to other fractions and to the cells that did not undergo to NEEGA-DG) are concentrated in the Fraction 2 in which the efficiency of the differentiation commitment is close to 100%. Fraction 1 contains low proliferating cells (cells with a low proliferation rate), morphologically heterogeneous cells, and a relevant amount of dead cells. The adipogenic differentiation potential of the cells isolated in Fraction 3 and Fraction 4 was significantly lower than cells in Fraction 2 and than cells that did not undergo to NEEGA-DF.

The method according to the present invention is able to isolate cell fractions with unequal differentiation potential correlated to different hierarchical level of stemness, and which can be used to improve their application in biomedical fields.

The invention claimed is:

1. A method for the fractionation of adherent stem cells from a living cell sample, comprising the following steps:
    a) preparing said living cell sample containing adherent stem cells suspended in a biocompatible fluid which is a mobile phase of a fractionation device;
    b) introducing said living cell sample into the fractionation device to perform non-equilibrium, gravity-assisted dynamic fractionation, wherein said introducing step is performed by a continuous flow of said mobile phase in a direction that is coincident with the direction of the Earth gravity field; wherein said continuous flow rate value is such that the injected cells present in said sample do not sediment at the accumulation wall of said fractionation device;
    c) eluting a plurality of sample fractions from said fractionation device wherein the fractionation channel is held in a horizontal position to make the gravitational field act perpendicularly to the carrier liquid flow; wherein said eluting step is performed at a mobile phase flow rate value for which the cells present in said sample do not come in contact with a wall of said fractionation device; and wherein said eluting step is performed at a mobile phase flow rate value for which the cells of said sample are swept down the channel at a given distance from said walls of said fractionation device; wherein in said step b) and in said step c) said introducing step and said eluting step are performed without stopping the flow, and at a flow rate value for which the cells present in said sample are not in contact with the accumulation wall;
    d) collecting fractions containing said stem cells from said plurality of sample fractions to produce fractionated stem cells.

2. The method according to claim 1, further comprising the step of isolating said fractionated stem cells after said step d).

3. The method according to claim 2, further comprising the step of performing post-fractionation selection after said isolating step.

4. The method according to claim 1, wherein said adherent stem cells are human stem cells.

5. The method according to claim 1, wherein said adherent stem cells are mesenchimal cells.

6. The method according to claim 4, wherein said living cell sample are isolated from the group consisting of bone marrow, dental pulp, adipose tissue, peripheral blood, placenta, umbilical cord, foetal membrane, amniotic membrane, chorial membrane, Wharton gel and lipoaspirates.

7. The method according to claim 1, further comprising the step of selecting said fractionated stem cells, expanding said fractionated stem cells, or committing said fractionated stem cells to differentiation.

8. The method according to claim 7, wherein said subsequent selection is performed.

9. The method according to claim 7, wherein said selecting step is performed using immunomarkers.

* * * * *